(12) United States Patent
Alland et al.

(10) Patent No.: US 6,458,566 B2
(45) Date of Patent: *Oct. 1, 2002

(54) METHOD OF IDENTIFICATION OF DIFFERENTIALLY EXPRESSED MRNA

(75) Inventors: David Alland, Dobbs Ferry, NY (US); Barry R. Bloom, Cambridge, MA (US); Igor Kramnik, Bronx, NY (US)

(73) Assignee: Albert Einstein College of Medicine of Yeshiva University, Bronx, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/178,098

(22) Filed: Oct. 23, 1998

(51) Int. Cl.[7] ................. C12D 19/34; C12Q 1/68; G01N 33/00; C07H 21/02; C07H 21/04
(52) U.S. Cl. .................. 435/91.2; 435/6; 435/91.1; 435/91.51; 436/94; 536/23.1; 536/24.3; 536/24.33
(58) Field of Search .............. 435/6, 91.1, 91.2, 435/91.51, 320.1, 252.1, 183, 287.2; 536/23.1, 24.3, 24.33, 25.3; 436/94

(56) References Cited

U.S. PATENT DOCUMENTS

| | | | |
|---|---|---|---|
| 5,360,893 A | * 11/1994 | Owen et al. | 530/350 |
| 5,641,658 A | * 6/1997 | Adams et al. | 435/91.2 |
| 5,804,382 A | * 9/1998 | Sytkowski et al. | 435/6 |

OTHER PUBLICATIONS

Green et al., Systematic screening of yeast artificial –chromosome libraries by use of the polymerase chain reaction. Proc. Natl. Acad. Sci. USA 87, 1213–1217, 1990.*
Plum et al., Induction of *Mycobacterium avium* gene expression following phagocytosis by human macrophages. Infection and Immunity, 62, 476–483, Feb. 1994.*
Stratagene Catalog (1994), pp. 154–157. Published by Stratagene Cloning Systems, 11011 North Torrey Pines Road, LA Jolla, CA 92037.*
Straus et al., Genomic subtraction for cloning DNA corresponding to deletion mutations. Proc. Natl. Acad. Sci. USA 87, 1889–1893, 1990.*
Hughes et al., Development of mycobacterial species–specific DNA probes by subtraction hybridization. FEMS Microbiology Lett. 156, 31–36, Nov. 1, 1997.*
Kinger et al., Identification and cloning of genes differentially expressed in the virulent strain of mycobacterium tuberculosis. Gene 131, 113–117, 1993.*
Riley et al., A novel, rapid method for the isolation of terminal sequences from yeast artificial chromosome (YAC) clones. Nucleic Acids Res. 18, 2887–2890, 1990.*
Straus et al., Genomic subtraction for cloning DNA corresponding to deletion mutations. Proc. Natl. Acad. Sci. USA 87, 1889–1893, Mar. 1990.*
Gingrich et al., partial CviJl digestion as an alterative approach to generate cosmid sublibraries for large scale sequencing projects. BioTechniques 21, 99–104, Jul. 1996.*
Maniatis et al., Molecular Cloning: A laboratory Manual, pp. 382–386, 1982, published by Cold Spring Harbor Laboratory, Box 100, Cold Spring Harbor, New York.*
Robinson et al., Isolation of maltose–regulated genes from the *Hyperthermophilic archaeum, Pyrococcus furisus,* by subtractive hybridization. Gene, 148, 137–141, 1994.*
Ray et al., Isolation and characterization of genes associated with chromosome–6 mediated tumor suppression in human malignant melanoma. Oncogene 12, 2527–2533, 1996.*

* cited by examiner

*Primary Examiner*—Ethan C. Whisenant
*Assistant Examiner*—Frank Lu
(74) *Attorney, Agent, or Firm*—Amster, Rothstein & Ebenstein

(57) ABSTRACT

The method provided by the present invention sets forth a novel combination of methods and principles which allows for the rapid and accurate isolation and identification of a large number of differentially expressed mRNAs.

10 Claims, 4 Drawing Sheets

SEQUENCE LISTING

```
<160> NUMBER OF SEQ ID NOS:   9

<210> SEQ ID NO 1
<211> LENGTH: 25
<212> TYPE: DNA
<213> ORGANISM: Artificial Sequence
<220> FEATURE:
<223> OTHER INFORMATION: Uniamp primer sequence
      (Clontech, Palo Alto, CA)

<400> SEQUENCE: 1
cctctgaagg ttccagaatc gatag                                           25

<210> SEQ ID NO 2
<211> LENGTH: 32
<212> TYPE: DNA
<213> ORGANISM: Artificial Sequence
<220> FEATURE:
<223> OTHER INFORMATION: Uniamp XhoI adapter sequence, top strand
      (Clontech, Palo Alto, CA)
```

-continued

```
<400> SEQUENCE: 2
cctctgaagg ttccagaatc gatagctcga gt                                    32

<210> SEQ ID NO 3
<211> LENGTH: 35
<212> TYPE: DNA
<213> ORGANISM: Artificial Sequence
<220> FEATURE:
<223> OTHER INFORMATION: Uniamp XhoI adapter sequence, bottom strand
      (Clontech, Palo Alto, CA)

<400> SEQUENCE: 3
actcgagcta tcgattctgg aaccttcaga ggttt                                 35

<210> SEQ ID NO 4
<211> LENGTH: 23
<212> TYPE: DNA
<213> ORGANISM: Artificial Sequence
<220> FEATURE:
<223> OTHER INFORMATION: reverse PCR iniA-specific primer

<400> SEQUENCE: 4
gcgctggcgg gagatcgtca atg                                              23

<210> SEQ ID NO 5
<211> LENGTH: 24
<212> TYPE: DNA
<213> ORGANISM: Artificial Sequence
<220> FEATURE:
<223> OTHER INFORMATION: reverse PCR iniA-specific primer

<400> SEQUENCE: 5
tgcgcagtcg ggtcacagga gtcg                                             24

<210> SEQ ID NO 6
<211> LENGTH: 19
<212> TYPE: DNA
<213> ORGANISM: Artificial Sequence
<220> FEATURE:
<223> OTHER INFORMATION: reverse PCR asd-specific primer

<400> SEQUENCE: 6
tcccgccgcc gaacaccta                                                   19

<210> SEQ ID NO 7
<211> LENGTH: 19
<212> TYPE: DNA
<213> ORGANISM: Artificial Sequence
<220> FEATURE:
<223> OTHER INFORMATION: reverse PCR asd-specific primer

<400> SEQUENCE: 7
ggatccggcc gaccagaga                                                   19

<210> SEQ ID NO 8
<211> LENGTH: 24
<212> TYPE: DNA
<213> ORGANISM: Artificial Sequence
<220> FEATURE:
<223> OTHER INFORMATION: reverse PCR 16S-specific primer

<400> SEQUENCE: 8
ggagtacggc cgcaaggcta aaac                                             24

<210> SEQ ID NO 9
```

```
<211> LENGTH: 24
<212> TYPE: DNA
<213> ORGANISM: Artificial Sequence
<220> FEATURE:
<223> OTHER INFORMATION: reverse PCR 16S-specific primer

<400> SEQUENCE: 9 cagacccga tccgaactga gacc                                              24
```

METHOD OF IDENTIFICATION OF DIFFERENTIALLY EXPRESSED MRNA

BACKGROUND OF THE INVENTION

The analysis of bacterial responses to environmental stimuli can provide valuable insights into cellular mechanisms (1–5). This approach is particularly well suited for studies of *Mycobacterium tuberculosis*, a pathogen that must adapt to a variety of hostile milieu including phagocytosis by macrophages and treatment with antibiotics. Differential gene expression in bacteria has been difficult to study because the absence of poly(A)$^+$ RNA complicates removal of abundant ribosomal rRNA from low-abundance mRNA. The number of differentially expressed genes that have been identified in bacteria has been limited (6–11), except under circumstances where large amounts of RNA can be obtained (12). It recently has become possible to monitor gene expression in multiple bacterial genes simultaneously by direct hybridization of total RNA to high-density DNA arrays (12). However, the large amounts of labeled RNA that must be hybridized to such arrays currently restricts their utility in many biologically relevant investigations. This problem is not resolved by amplification of samples with the PCR because it often is not possible to amplify complex mixtures of mRNA sequences while at the same time maintaining their relative proportions (13). Accordingly, an efficient and rapid method of identifying differentially expressed mRNA would aid tremendously in understanding gene differential gene expression.

SUMMARY OF THE INVENTION

The existing need for an efficient and rapid method of identifying differentially expressed mRNA is met by the method provided by the present invention. The method provided by the present invention sets forth a novel combination of methods and principles which allows for the rapid and accurate isolation and identification of a large number of differentially expressed mRNAs.

Additional objects of the invention will be apparent from the description which follows.

BRIEF DESCRIPTION OF THE FIGURES

FIG. 1A shows the generation of customized Amplification libraries (CAL). A cosmid library is screened for clones that contain ribosomal DNA sequences. Non-ribosomal cosmids are digested into similar sized fragments, gel purified, ligated to PCR adapters, and PCR amplified. FIG. 1B shows positive selection and hybridization. Reverse transcribed RNA samples are hybridized to a ribosomal DNA free CAL, washed, then amplified to generate PCR probes. FIG. 1C: The probes are labeled and hybridized to replicate colony arrays of genomic plasmid libraries. Colonies that hybridize with differing intensities to two PCR probes are selected for evaluation of differentially expressed sequences.

FIGS. 2A and 2B set forth the results of hybridization of PCR probes to genomic DNA and plasmid digests. DECAL was performed using RNA extracted from *M. tuberculosis* H37Rv cultures that were either untreated (INH−), or treated with isoniazid 1.0 μg/ml for 18 hours (INH+). FIG. 2A sets forth radiolabeled INH− cDNA (before positive selection with CAL), and radiolabled INH− and INH+ PCR probes (after positive selection with CAL and amplification) were hybridized to H37Rv genomic digests. The cDNA hybridized almost exclusively with a single band of ribosomal DNA. The INH− PCR probe and INH+ PCR probe both hybridized to multiple sequences in the *M. tuberculosis* chromosomal digests, but showed no hybridization to the ribosomal band. FIG. 2B sets forth Southern blots of *M. tuberculosis* H37Rv genomic DNA digested with PvuII, and PstI digests of six plasmids (P1–P6) that hybridized differentially to the PCR probes on colony array screening. Southern blots were hybridized with radio-labeled INH− PCR probe (top), or INH+ PCR probe (bottom). The INH− PCR probe hybridized exclusively to P6. The INH+ PCR probe almost exclusively to P1 and preferentially to P2 and P3. P4 and P5 did not hybridize differently to the two probes and are unlikely to code for isoniazid induced genes.

FIG. 3 shows the results of Induction of iniA after treatment with different antibiotics. Autoradiographs of a Northern blot containing RNA from *M. tuberculosis* cultures treated either with no antibiotics; isoniazid 0.01 μg/ml; isoniazid 0.1 μg/ml; isoniazid 1 μg/ml; ethambutol 5 μg/ml; streptomycin 5 μg/ml; and rifampin 5 μg/ml. The blots were hybridized first with an iniA DNA probe (top) to examine iniA induction; the blot was then stripped and re-hybridized with a 16S probe (bottom) to confirm equal RNA loading.

FIGS. 4A and 4B set forth the results of reverse transcription PCR of differentially expressed genes. FIG. 4A sets forth RNA was extracted from log phase *M. tuberculosis* strain Erdman either without (lanes 1–3) or with (4–6) isoniazid added to the bacterial cultures for the last 18 hours. RNA from both cultures was equalized by comparison of the 23S band intensity. RT PCR using three ten-fold dilutions of each RNA and either iniA, asd or 16S specific primers was performed. Induction of iniA and suppression of asd by isoniazid is demonstrated. The amount of 16S RT PCR product is similar for equivalent dilutions, indicating equal amounts of starting RNA. Lanes 7–8 are minus RT controls; and lane 9 a negative PCR control. FIG. 4B sets forth lack of iniA induction in an isoniazid resistant strain. Cultures of isogenic BCG strain ATCC35735 which is susceptible to isoniazid (lanes 1–6), or ATCC35747 which is resistant to isoniazid (lanes 7–12), were incubated either in the presence or absence of isoniazid for the last 18 hours. Three ten-fold dilutions of RNA extracted from each culture were tested by RT PCR for iniA induction. Induction is seen only in the INH susceptible strain. Lanes 13–16 are minus RT controls; and lane 17 a negative PCR control containing no added template.

FIG. 5 shows the limits to distinguishing differences between samples. Ten-fold decreasing amounts of in vitro transcribed *M. tuberculosis* inhA mRNA (tube 1 contained $1 \times 10^{11}$ molecules; tube 2, $1 \times 10^{10}$ molecules; tube 3, $1 \times 10^9$ molecules; tube 4, $1 \times 10^8$ molecules; tube 5, $1 \times 10^7$ molecules; tube 6, no added molecules), and four-fold increasing amounts of ask/asd mRNA (tube 1 contained no added molecules; tube 2, $4 \times 10^6$ molecules; tube 3, $1.7 \times 10^7$ molecules; tube 4, $6 \times 10^7$ molecules; tube 5, $2.5 \times 10^8$ molecules; tube 6, $1 \times 10^9$ molecules), were added to six tubes. Each tube also contained one microgram of BCG total RNA. DECAL was performed separately for each tube. The PCR probes were then hybridized to six Southern blots containing ask/asd DNA, inhA DNA, and *M. tuberculosis* H37Rv genomic digests. Autoradiography exposure was equalized to the hybridization intensity of the H37Rv bands.

DETAILED DESCRIPTION OF THE INVENTION

Figure 1:
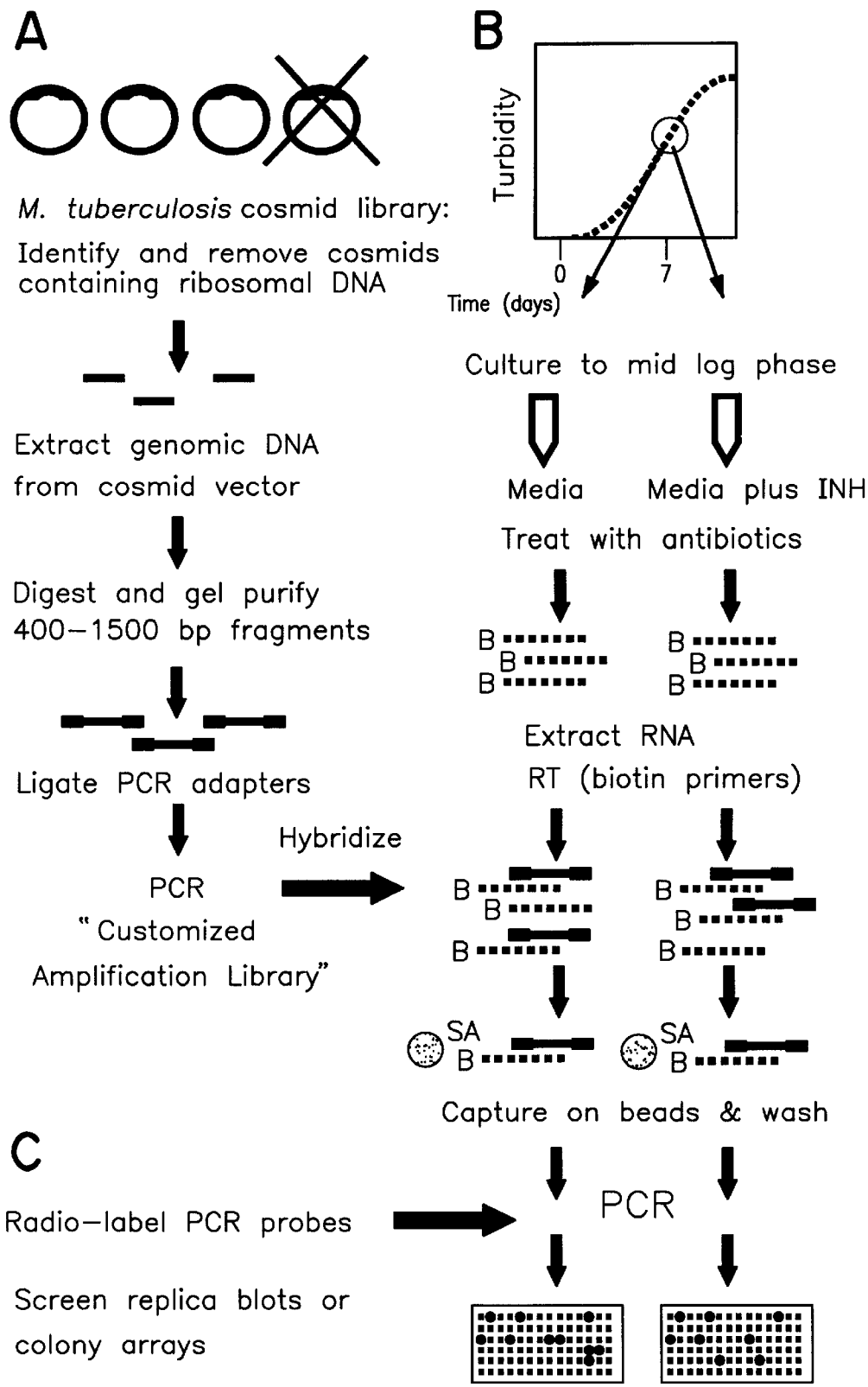
FIGS. 1A–1C: Schematic representation of differential expression using customized amplification libraries (DECAL).
Figure 2A:
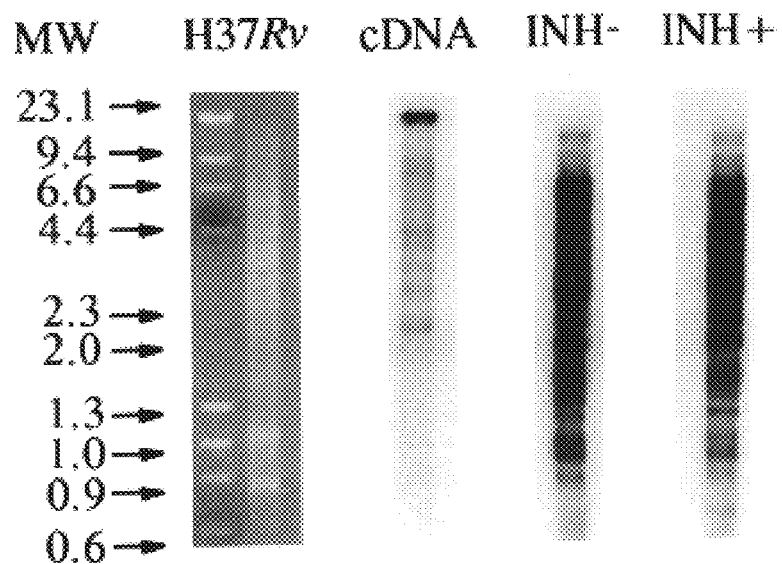
FIGS. 2A and 2B.
Figure 2B:
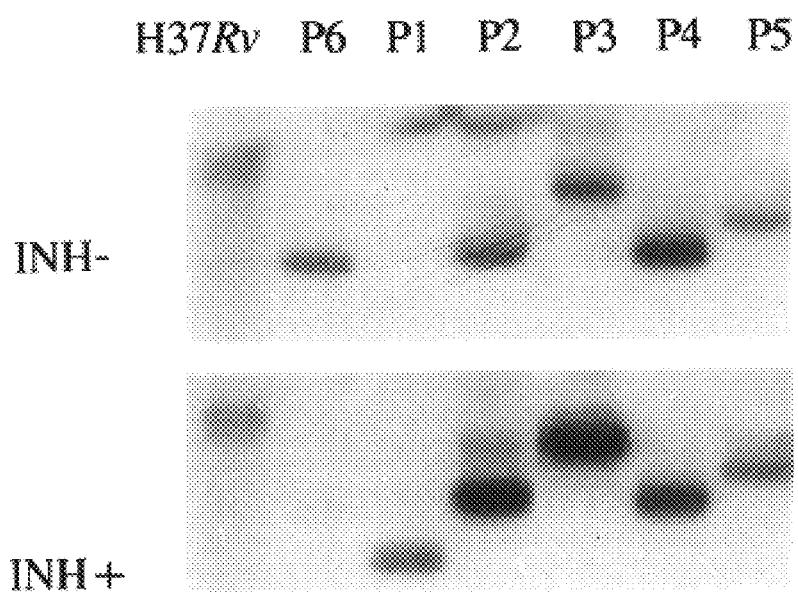
Figure 3:
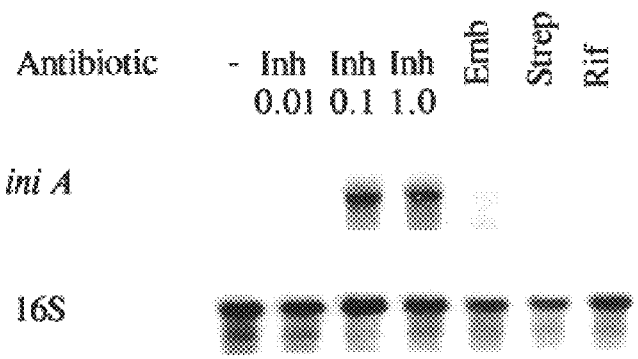
FIG. 3.

The present invention sets forth a novel approach for studying differences in mRNA expression, which the inventors have termed "differential expression using customized amplification libraries" (DECAL), that permits global comparisons of bacterial gene expression under varied growth conditions without a specific requirement for DNA arrays. The key feature of DECAL technology is the ability to amplify by PCR a complex mixture of expressed genes in a reproducible and representative manner without the confounding effects of rRNA or any other highly expressed gene product. The inventors have found that three steps are essential for this process: (i) removal of abundant sequences—in this case rRNA sequences; (ii) reduction in the complexity of the sequences and conversion of all cDNA sequences into fragments of similar size; and (iii) selecting sequences that amplify efficiently. DECAL accomplishes this by creating a customized amplification library (CAL) of genomic sequences that has been manipulated for optimal performance during PCR amplification. Instead of amplifying total cDNA sequences, cDNA is hybridized to an excess of CAL, nonhybridizing CAL sequences are removed and the remaining CAL sequences are amplified without altering their proportion representation. The amplified products derived from RNA samples can be hybridized to replicate colony blots or colony arrays, and the resulting hybridization patterns compare to determine the differentially expressed genes present in the original RNA samples. The inventors have herein demonstrated the applicability of the DECAL system to the study of *M. tuberculosis* gene expression in response to the antibiotic, isoniazid.

The present invention provides a method of making a customized nucleic acid library comprising nucleic acid sequences of interest and devoid of unwanted nucleic acids, said method comprising the steps of: (a) obtaining nucleic acid library containing the nucleic acid sequences of interest and unwanted nucleic acids; (b) screening said library for unwanted nucleic acids; and (c) removing said unwanted nucleic acids from said library resulting in a customized nucleic acid library comprising nucleic acid sequences of interest and devoid of unwanted nucleic acids. The customized nucleic acid library may comprise cDNA, RNA or genomic DNA. The cDNA, RNA or genomic DNA may be obtained from bacteria. In a preferred embodiment of the invention, the cDNA, RNA or genomic DNA is obtained from mycobacteria. The nucleic acid sequences of interest may be, for example, coding sequences, sequences corresponding to a particular class of genes and sequences of a particular family of genes. The unwanted nucleic acids are predetermined depending on the genes of interest. If a library containing the coding sequences of an entire genome is desired, the unwanted nucleic acids would be, for example, ribosomal RNA and other nucleic acids that occur with high frequency in cellular RNA. The library is screened for unwanted nucleic acids by contacting the library with nucleic acid probes complementary to the unwanted nucleic acids. The nucleic acid probes may be labeled with detectable markers which permits detection of unwanted nucleic acids upon hybridization with said probes. Non-limiting examples of detectable markers include fluorescence, enzymes, and radiolabeled markers, such as radiolabeled isotopes and biotin.

Further provided by the present invention is a method of making a customized nucleic acid amplification library comprising the steps of: (a) obtaining a nucleic acid library containing the nucleic acid sequences of interest and unwanted nucleic acids; (b) screening said library for unwanted nucleic acids; (c) removing said unwanted nucleic acids from said library resulting in a customized nucleic acid library comprising nucleic acid sequences of interest and devoid of unwanted nucleic acids; (d) excising the nucleic acid sequences of interest from the customized nucleic acid library, and (e) purifying the nucleic acid sequences of interest so excised; (f) ligating the purified nucleic acid sequences of interest into adapters; and (g) amplifying the purified nucleic acid sequences of interest to obtain a customized nucleic acid amplification library. The customized nucleic acid library may comprise cDNA, RNA or genomic DNA. The cDNA, RNA or genomic DNA may be obtained from bacteria. In a preferred embodiment of the invention, the cDNA, RNA or genomic DNA is obtained from mycobacteria. The nucleic acid sequences of interest may be, for example, coding sequences, sequences corresponding to a particular class of genes and sequences of a particular family of genes. The unwanted nucleic acids are predetermined depending on the genes of interest. If a library containing the coding sequences of an entire genome is desired, the unwanted nucleic acids would be, for example, ribosomal RNA and other highly expressed gene products. The library is screened for unwanted nucleic acids by contacting the library with nucleic acid probes complementary to the unwanted nucleic acids. The nucleic acid probes may be labeled with detectable markers which permits detection of unwanted nucleic acids upon hybridization with said probes. Non-limiting examples of detectable markers include fluorescence, enzymes, and radiolabeled markers, such as radiolabeled isotopes and biotin. The nucleic acid sequences of interest are purified to a particular size in order to generate a library of similarly sized fragments. In a particular embodiment of the invention, the nucleic acid sequences of interest are purified to a size between about 400 to about 1500 base pair fragments, although it is to be understood that other sizes of nulceic acids may be purified. Once purified, the nucleic acid sequences may be ligated to adapters for subsequent PCR, and may then be amplified to obtain a customized nucleic acid amplification library.

The present invention also provides a method of making a customized nucleic acid library comprising the steps of: (a) obtaining a nucleic acid library containing nucleic acid sequences of interest and unwanted nucleic acids; (b) amplifying the nucleic acid sequences of interest in the library to generate amplicons; and pooling amplicons or subsets thereof thereby obtaining a nucleic acid library containing nucleic acid sequences of interest devoid of unwanted nucleic acids. The separate, unpooled amplicons may be immobilized on a solid support. The solid support may be selected from the group consisting of, for example, cellulose, nitrocellulose, polystyrene, polypropylene, polysulfone, polyvinylidene fluoride, and polyethersulfone.

Further provided by the present invention is a method of detecting a nucleic acid sequence of interest in a sample containing nucleic acid comprising the steps of: (a) labeling the nucleic acid from the sample with a detectable marker; (b) contacting the nucleic acid so labeled with the customized nucleic acid amplification library produced by the methods described above under conditions permitting the nucleic acid so labeled to hybridize with the customized nucleic acid amplification library; and (c) detecting hybridization of the labeled nucleic acid with the customized nucleic acid amplification library.

Also provided by the present invention is a method of isolating a nucleic acid sequence of interest from a sample containing nucleic acid comprising the steps of: (a) labeling the nucleic acid from the sample with a detectable marker; (b) contacting the nucleic acid so labeled with the customized nucleic acid amplification library produced by the method described above under conditions permitting the nucleic acid so labeled to hybridize with the customized nucleic acid amplification library; (c) detecting hybridization of the labeled nucleic acid with the customized nucleic acid amplification library; and (d) isolating the hybridized nucleic acid so detected.

The present invention further provides a customized nucleic acid library comprising nucleic acid sequences of interest and devoid of unwanted nucleic acids. The customized nucleic acid library may comprise cDNA, RNA or genomic DNA. The cDNA, RNA or genomic DNA may be obtained from bacteria. In a preferred embodiment of the invention, the cDNA, RNA or genomic DNA is obtained from mycobacteria. The nucleic acid sequences of interest may be, for example, coding sequences, sequences corresponding to a particular class of genes and sequences of a particular family of genes. The library may contain the nucleic acid sequences of interest in vectors, such as cosmids or plasmids. The nucleic acid sequences of interest are amplified to form amplicons, which are then immobilized on a solid support. The solid support may be cellulose, nitrocellulose, polystyrene, polypropylene, polysulfone, polyvinylidene fluoride, or polyethersulfone. In a particular embodiment of the invention, the nucleic acid sequences of interest are purified to a size between about 400 to about 1500 base pair fragments, although it is to be understood that other sizes of nulceic acids may be purified.

Despite the many advantages of the DECAL technique, the use of colony arrays to detect PCR probe hybridization limits the ability of DECAL to perform truly global gene expression screens. Medium sized plasmid inserts usually contain sequences complementary to several open reading frames. This can result in decreased sensitivity for detecting differential mRNA expression when one gene on the plasmid is induced, but others on the same plasmid are repressed. Furthermore, it is laborious to evaluate every open reading frames on a differentially expressed plasmid in order to identify the actual differentially expressed gene.

The development of DNA array (chip) technology offers an elegant solution to this problem. DECAL can enhance the sensitivity of DNA array-based detection methods by providing probes that can be PCR amplified without significantly altering mRNA representation. DECAL generated PCR probes can be fluorescently labeled and hybridized to micro arrays containing short PCR amplicons from every M. tuberculosis open reading frame. The resulting fluorescent pattern will permit a clear determination of which CAL sequences represent differentially expressed genes. Using this approach, DECAL should extend the applicability of DNA arrays to investigations where limited amounts of initial RNA is available.

Adapt DECAL to enable hybridization with DNA microarrays. CAL sequences are unlikely to regularly cross hybridize to the probes that have been placed on DNA arrays. To ensure 100% cross hybridization with DNA microarrays, and to enable DNA arrays to "read" the results of subsequent DECAL experiments, we will create CALs using amplicons identical to those used in DNA array construction.

Determine the optimal CAL complexity, and create CALs containing more limited sequences for ultra sensitive screens. It is possible optimal proportional amplification will require CALs with reduced complexity compared to CALs constructed with the entire set of M. tuberculosis open reading frame amplicons. This will be investigated using CALs derived from amplicon subsets. In order to perform ultra sensitive differential expression screens, we will take advantage of the completely sequenced M. tuberculosis genome to design CALs with sequences limited to genes relevant to a specific area of investigation.

Develop DECAL for use with limiting amounts of bacterial RNA that is mixed with contaminating human/host sequences. DECAL can be performed with nanogram quantities of starting RNA; however, conditions have not been optimized for investigations where large amounts of contaminating foreign DNA or RNA is present. In experiments using M. tuberculosis RNA spiked into human and mouse RNA, we will determine the conditions that permit DECAL to be performed in the presence of large amounts of non-hybridizing nucleic acid sequences. One goal of this aim will be to determine the minimal amount of manipulations necessary to obtain sufficiently pure bacterial RNA for DECAL experiments.

Study gene expression in human sputum before and during early treatment. Gene expression will be investigated in order to determine the early changes that predict response to treatment. Microbial factors induced by the host immune response will also be investigated as potential vaccine candidates. This aim follows from the successful completion of aims 1–3. We will compare M. tuberculosis gene expression during human infection, by performing DECAL-DNA MICROARRAY assays of RNA isolated from sputum samples. Gene expression will be investigated with different stages and types of disease, different antibiotic treatments, and in patients with rapid and slow response to therapy.

Study gene expression in laminal models of infection. We will study and compare gene expression in mammalian host tissues in the early, middle and late stages of infection.

The present invention is described in the following Experimental Details Sections which is set forth to aid in the understanding of the invention, and should not be construed to limit in any way the invention as defined in the claims which follow thereafter.

Experimental Details Section

A. Materials and Methods

Libraries and plasmids. Cosmid libraries were constructed by ligation of Sau3A partial digests of M. tuberculosis H37Rv into pYUB328 (14). Plasmid libraries were constructed by ligation of complete PstI or SacI digests of M. tuberculosis H37Rv into pUC19 (15). The plasmid pUB124 was constructed by insertion of a 1.7 kb PstI fragment of the M. tuberculosis ask/asd operon containing the down stream portion of the M. tuberculosis ask gene and the complete asd gene into pKSII (16). The plasmid PET-inhA, containing an 800 base-pair fragment of the M. tuberculosis inhA gene inserted into the BamHI site of pET-23a+ (Novagen, Madison Wis.) was a kind gift of Dr. John Blanchard (Albert Einstein College of Medicine, Bronx N.Y.).

Creation of ribosomal free customized amplification libraries. One thousand cosmid library clones were inoculated into "master" 96 well microtiter plates containing L broth and ampicillin 50 µg/ml, transferred by a pronged "frog" onto Biotrans nylon membranes (ICN Pharmaceuticals, Costa Mesa, Calif.), and hybridized separately with [$\alpha^{32}$P] radiolabled (Megaprime labeling kit, Amersham, Arlington Heights, Ill.) PCR probes to M. tuberculosis ribosomal 5S, 16S, and 23S genes. Fourteen cosmids containing ribosomal DNA were identified; non-ribosomal cosmids were re-inoculated from master plates and individually cultured. Cosmids were extracted by SDS/alkaline lysis (17) in pools of 16. Cosmid DNA was pooled, digested with PacI, which does not restrict the M. tuberculosis genome, and insert DNA was purified from an agarose gel by electroelution. Approximately 1 µg of precipitated DNA was digested with AluI and 100 ng run on a 2% NuSieve GTG low melting point agarose gel (FMC Bioproducts, Rockland, Me.). Marker DNA was run simultaneously in a separate gel to avoid cross contamination of samples. The gels were aligned, and the section corresponding to 400–1,500 base pairs of the AluI digest was excised. Five µl of gel slice was ligated with 1 µl of Uniamp XhoI adapters 2 pmol/µl (Clonetech, Palo Alto, Calif.) in 20 µl total volume. Ten µl of the ligation was PCR amplified with 2 µl of 10 µM Uniamp primers (Clonetech), 1× vent polymerase buffer and 0.8 units of Vent (exo-) polymerase (New England Biolabs, Beverly, Mass.) in 100 µl total volume. After a five minute hot start, ten cycles of PCR with one minute segments of 95° C., 65° C., and 72° C., were followed by the addition of 3.2 units of Vent (exo-) polymerase and 27 additional cycles of 95° C. for one minute, 65° C. for two minutes, and 72° C. for three minutes. Uniamp primer sequence (SEQ ID NO:1): 5'-CCTCTGAAGGTTCCAGAATCGATAG-3'; Uniamp XhoI adapter sequence top strand (SEQ ID NO:2): 5'-CCTCTGAAGGTTCCAGAATCGATAGCTCGAGT-3'; bottom strand (SEQ ID NO:3): 5'-P-ACTCGAGCTATCGATTCTGGAACCTTCAGAGGTTT-3'.

RNA extraction. Mycobacterial cultures were grown to mid log phase in Middlebrook 7H9 media supplemented with OADC, 0.05% Tween 80, and cyclohexamide (18) (for some experiments antibiotics were added for the last 18 hours), pelleted, resuspended in chloroform/methanol 3:1, and vortexed for 60 seconds or until the formation of an interface. RNA was extracted with five volumes of Triazole (Life Technologies, Gaithersburg, Md.), the aqueous layer precipitated in isopropanol, redissolved in 4M GTC and extracted a second time with Triazole.

Positive selection. One µg of RNA was reverse transcribed with 7.7 µg biotin labeled random hexamers and biotin dATP (one tenth total DATP) using superscript II (Gibco BRL, Grand Island, N.Y.) at 50° C. for one hour, RNAse H was then added for one half hour at 37° C. Three hundred ng of CAL, 20 µg of salmon sperm DNA, and 20 µg of tRNA were added to the cDNA for a final volume of 150 µl. The sample was phenol/chloroform extracted twice, ethanol precipitated overnight, resuspended in 6 µl of 30 mM EPPS (Sigma), pH 8.0/ 3 mM EDTA, overlain with oil, and heated to 99° C. for 5 minutes, then 1.5 µl of 5 M NaCl preheated to 69° C. was quickly added (19). The sample was incubated at 69° C. for three to four days, then diluted with 150 µl of incubation buffer (1× TE, 1 M NaCl, 0.5% Tween 20) that had been preheated to 69° C., and 50 µl of washed, preheated streptavadin coated magnetic beads (Dynal, Oslo, Norway) were then added. The sample was then incubated at 55° C. with occasional mixing for 30 minutes, washed three times at room temperature and three times 30 minutes at 69° C. with 0.1% SDS, 0.2×SSC by placing the microfuge tubes into a larger hybridization tube in a rotating microhybridization oven (Bellco, Vineland, N.J.). The sample was then washed with 2.5 mM EDTA and eluted by boiling in 80 µl of water. PCR was performed as in the CAL preparation using 20 µl of sample.

Colony array hybridizations. Genomic plasmid library arrays were prepared by Genome Systems (St. Louis, Mo.) by robotically double spotting 9,216 colonies from the PstI and SacI plasmid libraries onto replicate nylon membranes. PCR probes were labeled by random priming with [$\alpha^{32}$P] dCTP (Megaprime labeling kit, Amersham) for at least 6 hours, hybridized to the colony arrays in Rapid-hyb buffer (Amersham), washed at 69° C. in 0.1× S.C., 0.1% SDS, and visualized by autoradiography. Double spotted colonies which hybridized at different intensities with two PCR probes were selected for further analysis.

Northern blots. Five µg of each RNA sample were analyzed by northern blot with Northern Max kits (Ambion, Austin, Tex.) in a 1% denaturing agarose gel, probed with inserts of differentially expressed plasmids labeled by random priming with [$\alpha^{32}$P] dCTP, and visualized by autoradiography.

Southern blots. Plasmid or genomic DNA was digested with restriction enzymes, subjected to electrophoresis in a 1% agarose gel and transferred by capillary action to Biotrans nylon membranes. The blots were hybridized and washed as in "colony array hybridizations" above, and visualized by autoradiography.

Reverse Transcription PCR. One microgram of RNA was reverse transcribed using the appropriate reverse PCR primer and superscript II at 50° C. For iniA and asd, three serial ten-fold dilutions of cDNA were made; 16S cDNA as diluted 1 in $10^6$, 1 in $10^7$, and 1 in $10^8$. PCR was performed with Taq polymerase and 1× PCR buffer (Gibco BRL) containing 2 mM $MgCl_2$ for 25 cycles annealing at 60° C. for iniA; 35 cycles annealing at 58° C. for asd; 25 cycles annealing at 63° C. for 16S. PCR products were analyzed on a 1.7% agarose gel, images were stored to disk by digital camera (Appligene, Pleasanton, Calif.), and the amounts of PCR product were calculated by densitometry (Imaging Software, National Institute of Health, Bethesda, Md.). Primers used for iniA: 5'-GCGCTGGCGGGAGATCGTCAATG-3' (SEQ ID NO:4), 5'-TGCGCAGTCGGGTCACAGGAGTCG-3'; (SEQ ID NO:5) for asd: 5'-TCCCGCCGCCGAACACCTA-3' (SEQ ID NO:6), 5'-GGATCCGGCCGACCAGAGA-3' (SEQ ID NO:7); for 16S: 5'-GGAGTACGGCCGCAAGGCTAAAAC-3' (SEQ ID NO:8), 5'-CAGACCCCGATCCGAACTGAGACC-3' (SEQ ID NO:9).

In vitro synthesis of inhA and askasd mRNA. Plasmid vectors PET-inhA (inhA mRNA synthesis) and pUB124 (ask/asd mRNA synthesis) were digested with HindIII and BstXI respectively to terminate transcription immediately downstream of the transcribed genes. Transcription was performed for 1 hour at 37° C. in 1× transcription buffer (Promega, Madison, Wis.) containing 500 ng of restricted plasmid DNA, 0.4 mM NTP's, 40 units RNAsin (Promega), and either 60 units of T7 RNA polymerase (Promega) for PET-inhA, or 60 units of T3 RNA polymerase (Promega) for pUB124. One unit of DNAse (DNAse R1Q, Promega) was then added to each tube and the reaction incubated for an additional 30 minutes. RNA was purified after DNAse treatment using RNeasy columns (Qiagen, Santa Clarita, Calif.), and quantitated by spectrophotometry. Complete plasmid DNAse treatment and mRNA synthesis was confirmed on both non-denaturing and denaturing agarose gels.

Adapt DECAL for detection with DNA arrays. CAL sequences are derived from size fractionated. AluI digests of M. tuberculosis genomic DNA. In contrasts, the probes present on DNA arrays are selected by computer for their uniqueness and their ability to be efficiently amplified by PCR. The CAL and DNA array sequences are unlikely to consistently cross hybridize. We will work in collaboration with investigators at Stanford University to resolve this problem. The goal will be to construct a CAL that can fully hybridize to DNA arrays. The amplicon sequences used in DNA array construction will be pooled and ligated with adapters to construct CALs. Currently, a single adapter sequence is used at both ends of the amplicons, but additional sensitivity may be obtained when two different adapter sequences are used. This type of CAL can be prepared by the simultaneous ligation of two adapter sequences followed by PCR with both complementary primers. Under the appropriate conditions, sequences will be preferentially amplified (Diatchenko et al., 1996). Initial experiments have been successful at making a single adapter CAL using amplicons pooled from 80% of the *M. tuberculosis* open reading frames. The representation of this CAL will be assessed by hybridization to the DNA arrays at Stanford University. Subsequent modifications in CAL preparation will be based on the results of the CAL-DNA array hybridization experiments. Improvements in CAL representation will be achieved by modifying adapter sequences, and adjusting the ligation and PCR conditions.

Determine the optimal CAL complexity, and create CALs containing more limited sequences for ultra sensitive screens. Proportional amplification of the approximately 4000 pooled DNA array amplicons may not be achievable in a single CAL preparation. Simultaneous amplification of this large number of sequences may be difficult to achieve even under the conditions of DECAL. It is also possible that specific sequences may be particularly resistant to amplification in a multiplex assay, or may amplify preferentially. DECAL is uniquely able to resolve these issues because the complexity of PCR amplification can be controlled by using greater or lesser numbers of sequences in CAL construction. A series of CALs will be created with increasing numbers of pooled amplicons. The optimal CAL complexity will be investigated in two ways. 1) For each CAL, the sample will be split into four, and separate DECAL experiments will be performed on an RNA sample that has been spiked with a number of different mRNA transcripts. The four resulting PCR will be hybridized to Southern blots containing the spiked sequences. The PCR probes will also be hybridized to DNA arrays. Proportional amplification will be assessed in a manner similar to the experiments outlined in preliminary data (FIGS. 2 and 3), and the consistency of amplification will be assessed by measuring the inter-assay variability of the four parallel DECAL experiments as they hybridize to the Southern blots and DNA arrays. 2) Large amounts of fluorescent RNA from *M. tuberculosis* cultured under two in vitro conditions (such as with and without isoniazid) will be hybridized directly to DNA arrays. DECAL experiments will be performed on these same RNA samples using CALs of increasing complexity. The proportional amplification and overall representation of each of the DECAL experiments will be assessed using the direct DNA array hybridization as a "gold standard." This will also permit the identification of "problem sequences" that are resistant to proportional amplification. These sequences will be omitted from subsequent CALs and will be incorporated into a separate low complexity CAL. If necessary, a number of reduced complexity CALs will be used in combination for subsequent studies.

It is not necessary to investigate the entire complement of *M. tuberculosis* expressed genes in every study. For example, studies of the in vivo bacterial response to isoniazid could initially be restricted to a subset (albeit large group) of genes involved in fatty acid biosynthesis. Other genes identified as regulated by isoniazid in vitro could also be included. Lower complexity CALs will be constructed that contain subsets of *M. tuberculosis* open reading frame amplicons specifically chosen for these types of studies. Because these CALs will contain many less sequences, each sequence should be amplified to a greater extent, permitting accurate investigations starting with very small amounts of material. These CALs will be carefully evaluated for overall sensitivity and proportional amplification as outlined above.

Develop DECAL for use with limiting amounts of bacterial RNA that is mixed with contaminating human/host sequences. Preliminary studies have demonstrated that DECAL can be performed with nanogram quantities of starting RNA. However DECAL has not been optimized for samples containing excess amounts of contaminating sequences will effect DECAL performance as the current assay is successful despite (because of) the inclusion 20 micrograms of tRNA and salmon sperm DNA in the positive selection step. However, samples obtained from solid organs may contain milligram quantities of host RNA. Different protocols will be investigated to determine the minimal amount of manipulations necessary to obtain sufficiently pure bacterial RNA for DECAL experiments. First *M. tuberculosis* RNA will be added into human RNA, and DECAL experiments will be performed as in aim 1 to estimate the amount of permissible contamination. Next, *M. tuberculosis* bacilli will be mixed with human and mouse samples, and different protocols of RNA extraction will be assessed for their impact on DECAL studies. In sputum, the benefit of DNAase and RNAase treatment prior to *M. tuberculosis* cell lysis and RNA extraction will be investigated. In mouse tissue, we will test the following protocol: Spleen, liver and lungs will be homogenized in mesh tubing containing PBS with 1% each of Trixton× 100 and deoxycholate to lese host tissue cells. This detergent treatment has no effect on the viability of the bacilli. issue suspensions will then be centrifuged after vigorous vortexing to obtain bacterial pellets. Four hundred micro liters of chloroform/methanol (3:1) will be added followed by three minutes of vortexing. Glass beads and two milliliters of Trizol Reagent (Life Technology) will then be added. The mixture will be vortexed for two minutes and 100 micro liters of $CHCl_3$ will be added. RNA will then be extracted as per the manufacturer's protocol and treated with DNAase. The RNA will then be recovered using RNeasy columns (Qiagen). This protocol has resulted in *M. tuberculosis* RNA of sufficiently good quality for RT PCR assays (Chan J, personal communication), and is likely to yield RNA that can be used in DECAL experiments.

Study gene expression in human sputum before and during early treatment. Microbial factors expressed during various stages of *M. tuberculosis* infection will be investigated using CALS composed of DNA array amplicons. Experiments will be performed under the conditions optimized in aims 1–3. Sputum samples will be obtained from patients before and during treatment under TBRU study protocols. Changes in gene expression will be investigated in both patients undergoing mono therapy and in patients receiving multi drug therapy. Both induction and suppression of genes will be investigated in order to determine the early changes that predict two month and four month culture negativity, and long term relapse free cures.

The second goal of this aim will be to determine if there is a relationship between bacterial gene expression and the type and extent of pulmonary tuberculosis. The host immune response clearly plays an important role in tuberculosis. However, primary bacterial factors may also influence disease progression, and these factors may in turn be modulated by host immune responses. Genes with increased expression during more advanced stages of disease may be potential vaccine candidates. Gene expression in patients with different stages of pulmonary infections that are enrolled in other TBRU studies will be compared. Sputum from relatively asymptomatic patients with pulmonary tuberculosis will be obtained as part of the household contact study. Preserved samples from the initial household case and other cases with more severe disease will also be used for comparison HIV positive and HIV negative subjects with similar stages of disease will also be examined.

Study gene expression in larninal models of infection. Animal models of infection will permit a more systematic study of gene expression during specific stages of disease. These investigations are important in that they may reveal new virulence determinants and vaccine candidates. Mice will be infected with H37rv both intravenously and via the aerosol route using the low dose infection model. Lung, liver and spleen will be harvested during early, middle and late stages of infection. The tissue will be processed as described in aim 3 and DECAL experiments performed.

B. Results

Creation of an *M. tuberculosis* customized amplification library (CAL). A representative genomic library of the entire *M. tuberculosis* genome was "customized" for proportional amplification by PCR (FIG. 1A). A critical requirement for the amplification library was that all DNA encoding rRNA genes had to be removed completely so that these highly abundant sequences could not confound proportional amplification in subsequent steps. This was performed by screening an *M. tuberculosis* cosmid library for rRNA gene sequences and removing all positive clones. The remaining rRNA free *M. tuberculosis* genomic sequences were excised from their cosmid vector and pooled. A second requirement was that the amplification library contain DNA sequences of relatively uniform size, and that their complexity be reduced in comparison to the entire *M. tuberculosis* genome. This was accomplished by restricting the excised inserts with AluI into small fragments and recovering the sequences between 400 and 1,500 base pairs in length by gel purification. The purified sequences were ligated to adapters for subsequent PCR. The final requirement for the amplification library was that all CAL sequences needed to be efficiently amplifiable by PCR. The AluI enzyme typically restricts *M. tuberculosis* open reading frame several times; we selected for the most efficiently amplifiable fragments by subjecting the library to a number PCR cycles prior to the subsequent hybridization steps.

Liquid hybridization and positive selection. During positive selection, cDNA is hybridized to the CAL, and CAL sequences that are non-complementary to the cDNA are removed (FIG. 1B). In order to identify the *M. tuberculosis* genes that were induced by isoniazid, *M. tuberculosis* was cultured to mid-log phase; the culture was then split and grown an additional 18 hours either in the absence (INH−) or presence (INH+) of isoniazid (1 μg/ml). Total cellular RNA was then extracted separately from both cultures, and reverse transcribed to biotin labeled cDNA. The biotin-cDNA was used to capture complementary CAL sequences on streptavidin beads. The beads were extensively washed, and the remaining CAL sequences were re-expanded by PCR. We term the products of this procedure "PCR probes". Despite the fact that the biotin cDNA from each sample was primarily ribosomal, neither INH− nor INH+PCR probes contained ribosomal sequences because no amplifiable ribosomal DNA was present in the CAL. However, each PCR probe hybridized to multiple non-ribosomal sequences when tested against an *M. tuberculosis* PvuII genomic digest (FIG. 2A) or assayed for hybridization to *M. tuberculosis* groES and hsp65 DNA, and randomly selected *M. tuberculosis* cosmids (data not shown).

Detection and evaluation of differential gene expression. Differentially expressed genes were determined by examining the differential hybridization patterns of the PCR probes (FIG. 1C). PCR probes derived from INH− and INH+ RNA samples were radiolabeled and hybridized to replica membranes containing arrays of colonies from an *M. tuberculosis* genomic library. Hybridization signals to most colonies were equal when small differences in background were accounted for, but a subset of colonies was found to hybridize more strongly to either the INH− or INH+ probe. Six colonies were selected for further evaluation; five hybridized more strongly with the INH+ probe (P1–P5) and one hybridized more strongly with the INH− probe (P6). Differential hybridization was confirmed for P1, P2, P3, and P6 by re-hybridizing the INH− and INH+ PCR probes to duplicate Southern blots of the excised plasmid inserts (FIG. 2B). P1 and P6 hybridized almost exclusively to the appropriate of the CR probes, while P2 and P3 hybridized to both probes but with different intensities. P4 and P5 were found not to hybridize differentially on secondary screen. The ends of the plasmid inserts were sequenced and aligned to the completely sequenced *M. tuberculosis* genome (20). P1 and P2, which encoded sequences that hybridized almost exclusively with the INH+ probe were homologous to a set of predicted proteins. P1 encoded a sequence identical to Rv0342, a large open reading frame that appeared to be the second gene of a probable three gene operon. This open reading frame was named iniA (isoniazid induced gene A), and the upstream open reading frame Rv0341, was named iniB. P2 encoded a sequence that was not complementary to P1, but that was identical to the third gene in the same probable operon Rv0343, this open reading frame was named iniC. A putative protein encoded by the iniA gene was found to contain a phosphopantetheine attachment site motif (21) suggesting that it functions as an acyl carrier protein. Both iniA and iniC lacked significant homology to other known genes but were 34% identical to each other. A sequence similarity search demonstrated that iniB had weak homology to alanine-glycine rich cell wall structural proteins (22). Northern blot analysis using excised inserts to probe total RNA from *M. tuberculosis* cultured in the presence or absence or different antibiotics verified that inia was strongly induced by isoniazid and ethambutol, drugs that act by inhibiting cell wall biosynthesis but not by rifampin or streptomycin, agents that do not act on the cell wall (FIG. 3). P3, which also encoded a sequence that preferentially hybridized to the INH+ probe contained a 5 kb insert spanning *M. tuberculosis* cosmids MTCYH10 and MTCY21D4. This region contained multiple small open reading frames, most with no known function. Northern blot analysis using the 5 kb insert as a probe confirmed that P3 preferentially hybridized to RNA from *M. tuberculosis* that had been cultured in the presence of isoniazid (data not shown). P6, which encoded a sequence hybridizing predominantly with the INH– probe was found to encode L-aspartic-β-semialdehyde dehydrogenase (asd). The asd gene is an important component of the diaminopimelate pathway required for biosynthesis of the peptidoglycan component of bacterial cell walls. Modulation of asd by a cell wall antibiotic such as isoniazid is not unexpected.

Figure 4A:
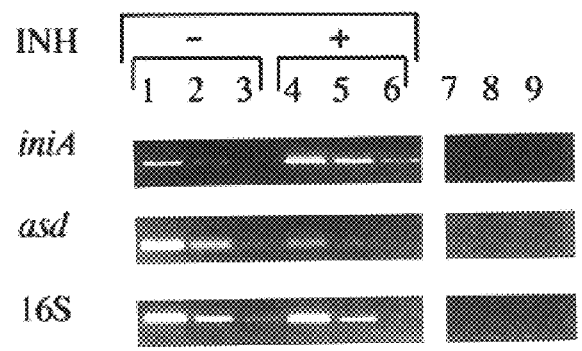
FIGS. 4A and 4B.
Figure 4B:
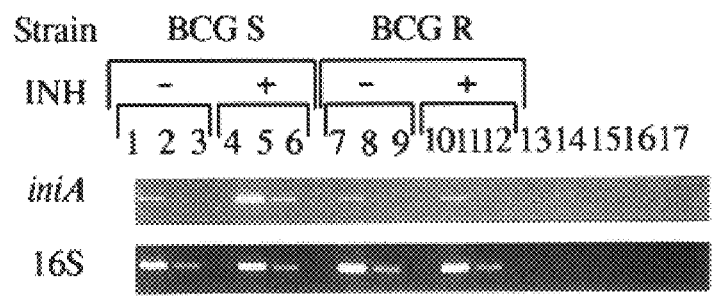

Reverse transcription (RT) PCR assays confirmed differential gene expression of both asd and iniA (FIG. 4A), as well as of iniB and iniC (data not shown). As predicted, iniA was strongly induced by isoniazid (70 fold induction by densitometry), while asd was repressed (17 fold). Induction of iniA was also tested in two isogenic strains of BCG that were either sensitive or resistant to isoniazid. The resistant phenotype was conferred by a mutation in katG which normally converts isoniazid from a prodrug to its active form (23). Induction of iniA was seen only in the susceptible BCG strain demonstrating the requirement for isoniazid activation (FIG. 4B).

Figure 5:
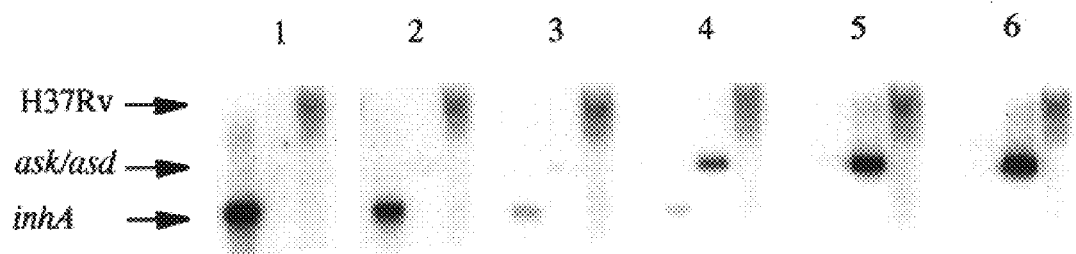
FIG. 5.

Detecting limited differences in gene expression and rare mRNAs. Most RNA subtraction techniques have a limited ability to detect differentially expressed genes that are present in both bacterial populations. We determined that the DECAL method can distinguish small differences in gene expression, and can detect rare mRNA sequences. Ten-fold dilutions of in vitro transcribed mRNA from the *M. tuberculosis* inhA gene were added to six tubes each containing one microgram of BCG total RNA (equivalent to approximately $1 \cdot 10^7$ bacilli). In vitro transcribed mRNA from the *M. tuberculosis* ask/asd operon was added to the same tubes in four-fold increasing amounts. The DECAL method was performed separately on each tube, and the relative proportions of amplified inhA and ask/asd CAL sequences were measured by hybridization of each PCR probe to identical Southern blots (FIG. 5). Decreasing inhA signal is apparent from $1 \cdot 10^{11}$ to $1 \cdot 10^7$ transcripts (1:20 w/w to 1:200,000 w/w) when normalized by equal hybridization to PvuII genomic digests of *M. tuberculosis* strain H37Rv. Increases in ask/asd signal can be detected beginning at $1.6 \cdot 10^7$ transcripts (1:64,000 w/w), and the signal clearly increased with each four-fold increase in added transcript. At lower amounts of added ask/asd or inhA mRNA, the signal merged with the background from the BCG RNA present in each tube. These results demonstrate that representative and proportional amplification is maintained in six separate samples, and confirm the ability of DECAL to detect small differences in gene expression for both high and low abundance mRNAs.

Figure 6:
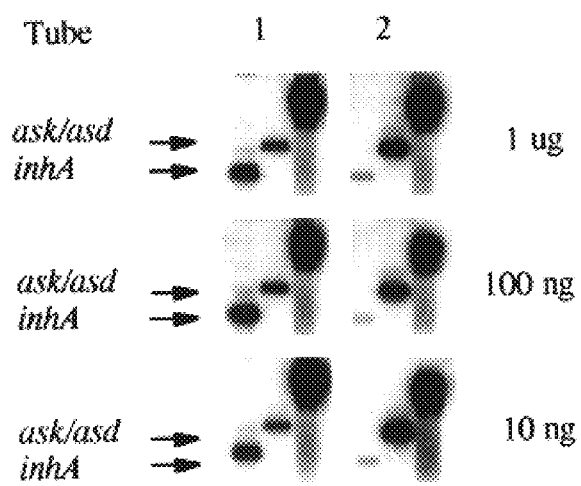
FIG. 6: Applying DECAL to small amounts of starting material. Ten-fold decreasing amounts ($1 \times 10^9$ and $1 \times 10^8$ molecules) of inhA mRNA, and four-fold increasing amounts ($1 \times 10^8$ and $4 \times 10^8$ molecules) of ask/asd mRNA were added to two tubes each containing one microgram of BCG total RNA. The tubes were reverse transcribed with biotin random primers, and serial ten-fold dilutions of the cDNA (equivalent to 1 µg, 100 ng and 10 ng of starting RNA) were subjected to the DECAL method. The resulting PCR probes were hybridized to duplicate Southern blots of a genomic *M. tuberculosis* H37Rv digest, inhA DNA, and ask/asd DNA, to assess for the presence of detectable differences in inhA and ask/asd signal. Autoradiography exposure was equalized to the hybridization intensity of the H37Rv bands.

Differential gene expression in small quantities of RNA. To investigate the sensitivity of the method, i.e. the minimum amount of starting RNA required, decreasing amounts of inhA mRNA, and increasing amounts of ask/asd mRNA were added to two tubes each containing one microgram of BCG total RNA. The tubes were reverse transcribed with biotin random primers, and serial ten-fold dilutions of the cDNA, equivalent to 1 µg, 100 ng and 10 ng of starting RNA, were assessed by DECAL for differences in inhA and ask/asd signals. The ten-fold differences in inhA mRNA and four-fold differences in ask/asd mRNA could be easily detected even in the highest cDNA dilution (FIG. 6). These results indicate that DECAL is able to detect small differences in mRNA with limiting amounts of RNA starting material. Furthermore, only 1% of the total PCR probe generated from each tube pair was used in the experiment, indicating that even lower limits of detection are likely.

C. Discussion

Current techniques to study differential gene expression in bacteria are limited by the problems associated with separating abundant rRNA sequences from mRNA, and by the difficulty of achieving proportional amplification of sequences in complex PCR reactions. The present study describes a simple and novel method for studying differential gene regulation between two bacterial populations. Differential gene expression is determined in a straightforward manner by comparing the relative intensity with which different PCR probes hybridize to individual colonies. Simultaneous detection of multiplegenes can be performed, identifying both mRNA sequences that are uniquely present in one sample, and those that are present in both samples but unequally represented. DECAL experiments are not dependent on polyA+ purified mRNA that is lacking in prokaryotes, and can be performed without customized arrays, and without knowledge of the entire bacterial sequence. DECAL may also enhance the sensitivity of DNA array-based detection methods by providing probes that can be PCR amplified without significantly altering mRNA representation. DECAL should extend the applicability of DNA arrays to investigations where limited amounts of initial RNA is available.

Unlike total RNA or cDNA, customized amplification libraries can be manipulated in a variety of ways to fulfill specific requirements. For example, sets of CALs could be constructed that contain only a subset of the entire genome. This could be easily performed by using different restriction digests and more limited size fractionation during CAL preparation. CALs with more limited sequence representation might be advantageous when studying gene expression in eukaryotic organisms with larger genomes. While CALs require several weeks to construct, once prepared they are available for many experiments. DECAL also has the unique ability to allow unwanted RNA to be discarded without RNA subtraction because only mRNA sequences that have complementary CAL sequences can be represented in the final PCR probe. This property makes DECAL ideally suited for in vivo investigations where RNA samples may contain contaminating sequences from host tissue.

DECAL is critically dependent on removal of all non-hybridizing CAL sequences. This problem was solved by the development of a highly efficient wash protocol. During CAL preparation, some genes flanking the ribosomal gene sequences are removed along with the ribosomal coding cosmids, thus inevitably some genes flanking the ribosomal gene sequences are removed along with the ribosomal coding cosmids. However, cosmids with overlapping inserts for CAL construction were used; therefore, only a limited number of genes falling between the two Sau3A sites most proximal to the ribosomal DNA sequences will have been removed completely. Some genes may not have been digested into the 400 to 1,500 base pair fragments used in CAL construction, or may have been lost during the pre-hybridization amplification step of CAL synthesis. A more complete CAL could be constructed by combining several digests made with different restriction enzymes.

DECAL was applied to study gene expression in *M. tuberculosis* after treatment with the antibiotic isoniazid. Isoniazid has long been a first line drug for the treatment of tuberculosis (24) however, its full mechanism of action remains to be established (25, 26). The discovery by the inventors of genes that are induced by both isoniazid and ethambutol, two cell wall active antibiotics that have different mechanisms of action (23, 25–28) adds further complexity to this issue. The role of the iniA operon is not well understood. The phosphopantetheine attachment site motif encoded by the iniA gene suggests that it encodes an acyl carrier protein, however it may also have other functions.

Another acyl carrier protein acpM has been described recently that both binds to and is induced by isoniazid (26). However no gene in the iniA operon has significant homology to any gene in the operon containing acpM or to the antigen 85 complex that has also been shown to be induced by isoniazid (29). Unlike these genes, only iniA is induced by both isoniazid and ethambutol. The inventors speculate that the iniA operon may be induced as a protective response to cell wall mediated cellular injury. If this is the case, agents capable of blocking inia, inib, or iniC function would be expected to act synergistically with isoniazid and other cell wall active antibiotics to kill *M. tuberculosis*.

REFERENCES

1. Sanders, C. C. (1987) *Annu. Rev. Microbiol.* 41, 573–593.
2. Miller, J. F., Mekalanos, J. J., & Falkow, S. (1989) *Science* 243, 916–922.
3. Korfmann, G., Sanders, C. C., & Morland, E. S. (1991) *Antibicrob. Agents Chemother.* 35, 358–364.
4. Beattie, D. T., Shahin, R., & Mekalanos, J. J. (1992) *Infect. Immun.* 60, 571–577.
5. Stragier, P., & Losick, R. (1996) *Annu. Rev. Genet.* 30, 297–341.
6. Mathiopoulos, C., & Sonenshein, A. L. (1989) *Mol. Microbiol.* 3, 1071–1081.
7. Wang, Z., & Brown, D. D. (1991) *Proc. Natl. Acad. Sci. USA* 88, 11505–11517.
8. Kinger, K. A., & Tyagi, J. S. (1993) *Gene* 131, 113–117.
9. Plum, G., & Clark-Curtis, J. E. (1994) *Infect. and Immun.* 62, 476–483.
10. Wong, K.K., & McClelland, M. (1994) *Proc. Natl. Acad. Sci. USA* 91, 639–643.
11. Utt, E. A., Brousal, J. P., Kikuta-Oshima, L. C., & Quinn, F. D. (1995) *Can. J. Microbiol.* 41, 152–156.
12. de Saizieu, A., Certa, U., Warrington, J., Gray, C., Keck, W., & Mous, J. (1998) *Nature Biotech.* 16, 45–48.
13. Marshall, A., & Hodgson, J. (1998) *Nature Biotech.* 16, 27–31.
14. Balasubramanian, V., Pavelka, M. S., Jr., Bardarov, S. S., Martin, J., Weisbrod, T. R., McAdam, R. A., Bloom, B. R., & Jacobs, W. R., Jr. (1996) *J. Bacteriol.* 178, 273–279.
15. Miller, L. P., Crawford, J. T., & Shinnick, T. M. (1994) *Antibicrob. Agents Chemother.* 38, 805–811.
16. Cirillo, J. D., Weisbrod, T. R., Pascopella, L., Bloom, B. R., & Jacobs, W. R., Jr. (1994) *Mol. Microbiol.* 11, 629–639.
17. Maniatis, T., Fritsch, E. F., & Sambrook, J. (1989) *Molecular Cloning: a Laboratory Manual* (Cold Spring Harbor Lab. Press, Cold Spring Harbor, N.Y.), 2nd ed.
18. Jacobs, W. R., Kalpana, G. V., Cirillo, J. D., Pascopella, L., Snapper, S. B., Udani, R. A., Jones, W., Barletta, R. G., & Bloom, B. R. (1991) 204, 537–555.
19. Lisitsyn, N., Lisitsyn, N., & Wigler, M. (1993) *Science* 259,946–951.
20. Cole, S. T., Brosch, R., Parkhill, J., Garnier, T., Churcher, C., Harris, D., Gordon, S.V., Eiglmeier, L., Gas, S., et al. (1998) *Nature* 393, 537–544.
21. Bairoch, A., Bucher, P., & Hofmann, K. (1997) *Nucleic Acids Res.* 25, 217–221.
22. Altschul, S. F., Madden, T. L., Schaffer, A. A., Zhang, J., Zhang, Z., Miller, W., & Lipman, D. J. (1997) *Nucleic Acids Res.* 25,3389–3402.
23. Zhang, Y., Heym, B., Allen, B., Young, D., & Cole, S. (1992) *Nature 358, 591–593.*
24. Bass, J. B., Jr., Farer, L. S., Hopewell, P. C., O'Brien, R., Jacobs, R. F., Ruben, F., Snider, D. E., Jr., & Thornton, G. (1994) *Am. J. Respir. Crit. Care. Med.* 149, 1359–1374.
25. Banerjee, A., Dubnau, E., Quemard, A., Balasubramanian, V., Um, K. S., Wilson, T., Collins, D., de Lisle, G., Jacobs, W. R., Jr. (1994) *Science* 263, 227–230.
26. Mdluli, K., Slayden, R. A., Zhu, Y., Ramaswamy, S., Pan, X., Mead, D., Crane, D. D., Musser, M. J., & Barry, C. E., III. (1998) *Science. 280, 1607–1610.*
27. Belanger, A. E., Besra, G. S., Ford, M. E., Mikusova, K., Belisle, J. T., Brennan, P. J., Inamine, J. M. (1996) *Proc. Natl. Acad. Sci. USA* 93, 11919–11924.
28. Telenti, A., Philipp, W. J., Sreevatsan, S., Bemasconi, C., Stockbauer, K. E., Wieles, B., Musser, J. M., Jacobs, W. R., Jr. (1997) *Nat. Med.* 3, 567–570.
29. Garbe, T. R., Hibler, N. S., & Deretic, V. (1996) 40, 1754–1756.

What is claimed is:

1. A method of making a customized nucleic acid amplification library comprising the steps of:
   (a) obtaining a nucleic acid library containing nucleic acid sequences of interest and rRNA gene sequences, wherein the sequences are in vectors;
   (b) screening said library for rRNA gene sequences;
   (c) removing said rRNA gene sequences from said library resulting in a customized nucleic acid library comprising nucleic acid sequences of interest and devoid of rRNA gene sequences;
   (d) excising the nucleic acid sequences of interest from the customized nucleic acid library and restricting said nucleic acid sequences so excised to obtain restricted nucleic acid sequences of 400–1500 bp in length;
   (e) purifying the restricted nucleic acid sequences;
   (f) ligating the purified nucleic acid sequences into adapters; and
   (g) amplifying the purified nucleic acid sequences to obtain a customized nucleic acid amplification library.

2. The method of claim 1, wherein the customized nucleic acid library comprises cDNA or genomic DNA.

3. The method of claim 1, wherein the cDNA or genomic DNA is obtained from bacteria.

4. The method of claim 1, wherein the nucleic acid sequences of interest are coding sequences.

5. The method of claim 1, wherein the library is screened for rRNA gene sequences by contacting the library with nucleic acid probes complementary to the rRNA gene sequences.

6. The method of claim 5, wherein the nucleic acid probes are labeled with detectable markers which permits detection of rRNA gene sequences upon hybridization with said probes.

7. A method of detecting a nucleic acid sequence of interest in a sample containing nucleic acid comprising the steps of:
   (a) labeling the nucleic acid from the sample with a detectable marker;
   (b) contacting the nucleic acid so labeled with the customized nucleic acid amplification library produced by the method of claim 1 under conditions permitting the nucleic acid so labeled to hybridize with the customized nucleic acid amplification library; and
   (c) detecting hybridization of the labeled nucleic acid with the customized nucleic acid amplification library.

8. A method of isolating a nucleic acid sequence of interest from a sample containing nucleic acid comprising the steps of:
   (a) labeling the nucleic acid from the sample with a detectable marker;
   (b) contacting the nucleic acid so labeled with the customized nucleic acid amplification library produced by the method of claim 1 under conditions permitting the nucleic acid so labeled to hybridize with the customized nucleic acid amplification library; and
   (c) isolating the hybridized nucleic acid so detected.

9. The method of claim 1, wherein the vectors are cosmid vectors.

10. The method of claim 1, wherein the screening of step (b) is by hybridization of the vectors in the library to a labeled rRNA sequence probe and identification and removal of the labeled vectors.

* * * * *